(12) United States Patent
Amir et al.

(10) Patent No.: US 9,536,042 B2
(45) Date of Patent: Jan. 3, 2017

(54) USING RNAI IMAGING DATA FOR GENE INTERACTION NETWORK CONSTRUCTION

(71) Applicant: International Business Machines Corporation, Armonk, NY (US)

(72) Inventors: Arnon Amir, Saratoga, CA (US); Tanveer Fathima Syeda-Mahmood, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 592 days.

(21) Appl. No.: 13/834,742

(22) Filed: Mar. 15, 2013

(65) Prior Publication Data

US 2014/0270455 A1   Sep. 18, 2014

(51) Int. Cl.
| | | |
|---|---|---|
| G06F 19/00 | (2011.01) | |
| G06F 19/10 | (2011.01) | |
| G06F 19/18 | (2011.01) | |
| G06F 19/12 | (2011.01) | |
| G06K 9/00 | (2006.01) | |

(52) U.S. Cl.
CPC ............... *G06F 19/18* (2013.01); *G06F 19/12* (2013.01); *G06K 9/00* (2013.01)

(58) Field of Classification Search
None
See application file for complete search history.

(56) References Cited

U.S. PATENT DOCUMENTS

| | | |
|---|---|---|
| 6,203,987 B1 | 3/2001 | Friend et al. |
| 7,181,365 B2 | 2/2007 | Inoue et al. |
| 7,496,550 B2 | 2/2009 | Rice et al. |
| 7,542,854 B2 | 6/2009 | Kelkar et al. |
| 2006/0263798 A1 | 11/2006 | Huynh et al. |
| 2008/0125583 A1 | 5/2008 | Rigoutsos et al. |
| 2010/0186119 A1 | 7/2010 | Finer et al. |

FOREIGN PATENT DOCUMENTS

WO   03/068928   8/2003

OTHER PUBLICATIONS

Markowetz and Spang (BMC Bioinformatics (2007) vol. 8(Suppl. 6):S5 (e 1-17)).*
Conrad et al. (Genome Research (2004) vol. 12, pp. 1130-1136.*
Misselwitz et al. (BMC Bioinformatics (2010) vol. 11:30 (E-pp. 1-13).*
Takahashi et al., Quantitative and Temporal Analysis of Gene Silencing in Tumor Cells Induced by Small Interfering RNA or Short Hairpin RNA Expressed From Plasmid Vectors, Journal of Pharmaceutical Sciences, vol. 98, No. 1, pp. 74-80, Jan. 2009.
Rahmanto et al., Chapter 4: Identification of Distinct Changes in Gene Expression After Modulation of Melanoma Tumour Antigen p97 (Melanotransferrin) in Multiple Models In Vitro and In Vivo, Carcogenesis 28(10): 2172-83, IF 2006:5.3., 2007.

* cited by examiner

*Primary Examiner* — Lori A Clow
(74) *Attorney, Agent, or Firm* — Lieberman & Brandsdorfer, LLC

(57) ABSTRACT

Embodiments of the invention relate to a constructing a gene interaction network. Tools are provided to compute a gene relationship measure based upon cellular images, and to rank image collections having a similar morphology. The ranking is based upon capturing similarity within the ranked collection by modeling a three dimensional shape of a cellular image stack. The graph is constructed for related images stacks. Nodes in the graph represent genes, and edges drawn between the nodes represent corresponding image stacks in a commonly ranked list. Accordingly, the graphical representation mathematically and visually connects respective genes.

10 Claims, 4 Drawing Sheets

USING RNAI IMAGING DATA FOR GENE INTERACTION NETWORK CONSTRUCTION

BACKGROUND

This invention relates to gene interaction network construction. More specifically, the invention relates to inferring genotypical similarity from RNA Interference (RNAi) imaging data and its use in gene interaction network construction.

Research in the area of biotechnology is constantly growing and evolving. Construction of a gene interaction network is sought after to provide knowledge and understanding of biological processes and diseases, and in the future may help with the identification of therapeutic compounds. Building gene interaction networks and predicting functions of genes poses a significant challenge to scientists. Model organisms are known to contain a large number of genes whose functions are unknown. Pathways, such as those for apoptosis and mitochondrial biogenesis, have only been partially identified. The rate of gene function determination significantly lags behind gene sequencing, thereby causing a backlog of genetic sequences in search of a function.

A number of approaches have been used to reveal genetic pathways, ranging from traditional low-throughput genetic screens based on phenotypes to microarray experiments that reveal gene expression similarity under various experimental conditions. In particular, visual assays using microscopy represents a medium for phenotypically assessing gene function that is complementary to microarrays. With the increasing use of RNAi, through modern three dimensional restorations or confocal microscopy and high throughput imaging platforms, large amounts of image based data has become available. Microscopic imaging is a powerful tool that allows functions and aspects of cells to be studied via morphological changes, such as changes in size and shape of cells, number of subcellular organelles and structures, or the redistribution of specific proteins within the cell.

BRIEF SUMMARY

This invention comprises a system and article for construction of a gene interaction network. In one aspect of the invention, recorded images of groups of cells associated with a first set of genes are received. Each of the groups of cells is received by knocking down one or more genes from a second set of genes. The first and second set of genes includes common genes. For each pair of genes in the second set, a gene relationship measure based on cellular images is computed. The computation uses morphological similarity measure between corresponding groups of cells. Images having a similar morphology are ranked. The ranking includes modeling a three dimensional shape of a cellular image stack produced by knocking down respective genes. Finally, a graph is constructed for related image stacks. Each gene is represented in the graph as a node, and edges are drawn between the nodes based on image ranking in a commonly ranking list.

Other features and advantages of this invention will become apparent from the following detailed description of the presently preferred embodiment of the invention, taken in conjunction with the accompanying drawings.

BRIEF DESCRIPTION OF THE SEVERAL VIEWS OF THE DRAWINGS

The drawings referenced herein form a part of the specification. Features shown in the drawings are meant as illustrative of only some embodiments of the invention, and not of all embodiments of the invention unless otherwise explicitly indicated. Implications to the contrary are otherwise not to be made.

DETAILED DESCRIPTION

Figure 1:
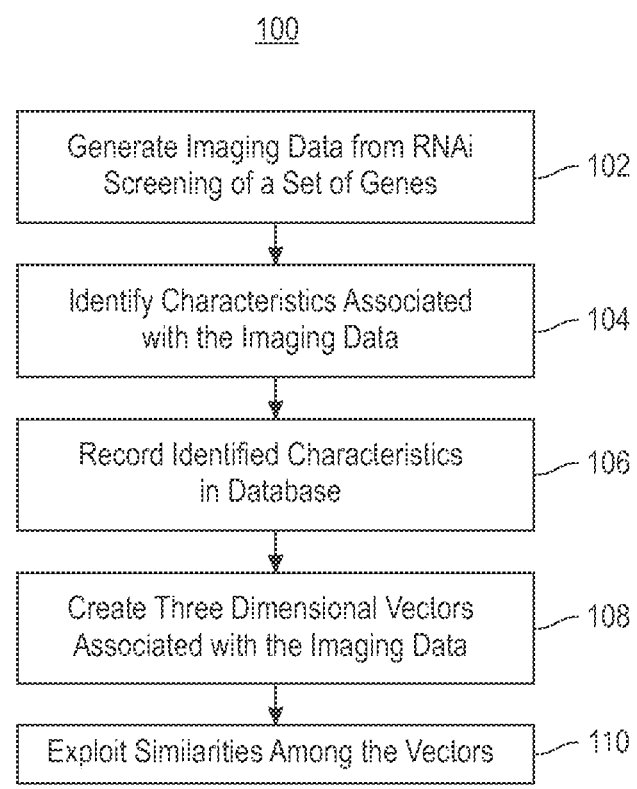
FIG. 1 is a flow chart illustrating a process for identifying image based similarities in data associated with a set of genes.

It will be readily understood that the components of the present invention, as generally described and illustrated in the Figures herein, may be arranged and designed in a wide variety of different configurations. Thus, the following detailed description of the embodiments of the apparatus, system, and method of the present invention, as presented in the Figures, is not intended to limit the scope of the invention, as claimed, but is merely representative of selected embodiments of the invention.

The functional unit described in this specification have been labeled as having managers and director(s). A functional unit may be implemented in programmable hardware devices such as field programmable gate arrays, programmable array logic, programmable logic devices, or the like. The functional unit may also be implemented in software for processing by various types of processors. An identified functional unit of executable code may, for instance, comprise one or more physical or logical blocks of computer instructions which may, for instance, be organized as an object, procedure, function, or other construct. Nevertheless, the executable of an identified functional unit need not be physically located together, but may comprise disparate instructions stored in different locations which, when joined logically together, comprise the functional unit and achieve the stated purpose of the functional unit.

Indeed, a functional unit of executable code could be a single instruction, or many instructions, and may even be distributed over several different code segments, among different applications, and across several memory devices. Similarly, operational data may be identified and illustrated herein within the functional unit, and may be embodied in any suitable form and organized within any suitable type of data structure. The operational data may be collected as a single data set, or may be distributed over different locations including over different storage devices, and may exist, at least partially, as electronic signals on a system or network.

Reference throughout this specification to "a select embodiment," "one embodiment," or "an embodiment" means that a particular feature, structure, or characteristic described in connection with the embodiment is included in at least one embodiment of the present invention. Thus, appearances of the phrases "a select embodiment," "in one embodiment," or "in an embodiment" in various places throughout this specification are not necessarily referring to the same embodiment.

Furthermore, the described features, structures, or characteristics may be combined in any suitable manner in one or more embodiments. In the following description, numerous specific details are provided, such as examples of managers and directors, including but not limited to an image manager, a graph manager, and a director, to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

The illustrated embodiments of the invention will be best understood by reference to the drawings, wherein like parts are designated by like numerals throughout. The following description is intended only by way of example, and simply illustrates certain selected embodiments of devices, systems, and processes that are consistent with the invention as claimed herein.

In the field of biotechnology it is known to subject genes to analysis under various conditions. This analysis is known as a visual assay. More specifically and as disclosed herein, visual data is employed to guide construction of a gene interaction network. Three dimensional morphological and shape descriptors are extracted from images of cells. Characteristics of the changes in the cells are computed. These characteristics include, but are not limited to, cell count, volume, higher moments, surface area, three dimensional textures, and edges. Based upon the computations, features of the cells and their morphological similarity among images of cells are exploited.

Gene expression data associated with the visual data provides a positive indication of the effect of a gene, i.e. the effect on the cells when a gene is expressed. A complementary piece of information is available through gene knockdown experiments in which a gene is removed from the cell (gene silenced) and the effect on the cells is studied. The process is called RNAi (RNA interference) where for each three dimensional segmented region of the cells, changes in the cell or nucleus appearance induced by a particular RNAi is measured. RNAi is the introduction of double-stranded ribonucleic acid (RNA) into a cell to inhibit the expression of a gene. The gene knockdown experiments are typically performed through visual assays. Imaging devices, including photon microscopes and high resolution electron tomography, are used to study the changes in cellular morphology. Accordingly, the gene knockdown information can be used as a complementary cue to infer a network.

FIG. 1 is a flow chart (100) illustrating a process for identifying image based similarities in data associated with a set of genes. Prior to assessing similarities, imaging data is generated from RNAi screening of a set of genes (102). As imaging data may include large volumes of data, characteristics associated with the imaging data are identified (104) and recorded in a database (106). In one embodiment, the recorded image data is received from a third party. More specifically, the image data is three dimensional data including three dimensional morphological and shape descriptors from images of cells. Three dimensional feature vectors are created (108), and similarities among the vectors are exploited (110). Accordingly, image similarity is computed from RNAi screening of a set of genes.

Figure 2:
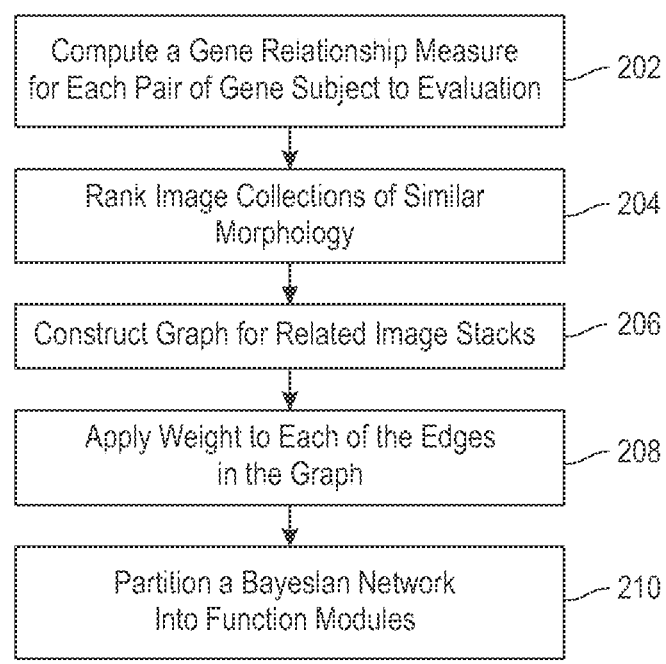
FIG. 2 is a flow chart illustrating a process for constructing a gene interaction network based upon the identified image based similarities.

Once the similarities among the genes subject to evaluation are identified, a graph is constructed to illustrate the relationship among the genes and their associated similarities. FIG. 2 is a flow chart (200) illustrating a process for construction of the above-described graph. For each pair of genes subject to evaluation, a gene relationship measure is computed (202). In one embodiment, the measure is based upon cellular images using a morphological similarity measure between corresponding groups of cells. Based upon the computation, image collections of similar morphology are ranked (204). More specifically, the ranking includes capturing the similarity of the measurement by modeling a three dimensional shape of a cellular image stack produced by knocking down respective genes. In one embodiment, a three dimensional feature vector is employed as a numerical measurement of the image data. The ranking of the similarity among the images supports identification of relationships among images. A graph is constructed for related images stacks thereby connecting the respective genes in a mathematical and graphical relationship (206). In one embodiment, the constructed graph is a directed acyclic graph formed by a collection of vertices and directed edges. The aspect of generating a graph includes each vertex in the graph representing a gene, and drawing directed edges between each of the vertices in the graph. Once the graph is created, a weight is applied to each of the edges in the graph (208). The weight reflects a similarity score and rank in a list of matches for a three dimensional query stack generated for a particular gene. In addition, a Bayesian network representing the probable relationship between the genes as represented in the graph is partitioned into functional modules (210); the modules correspond to genes that are part of the same biological pathway based on morphological similarity. Accordingly, the graph is a visual representation of the identified genes whose corresponding image stacks are in a commonly ranked list.

Figure 3:
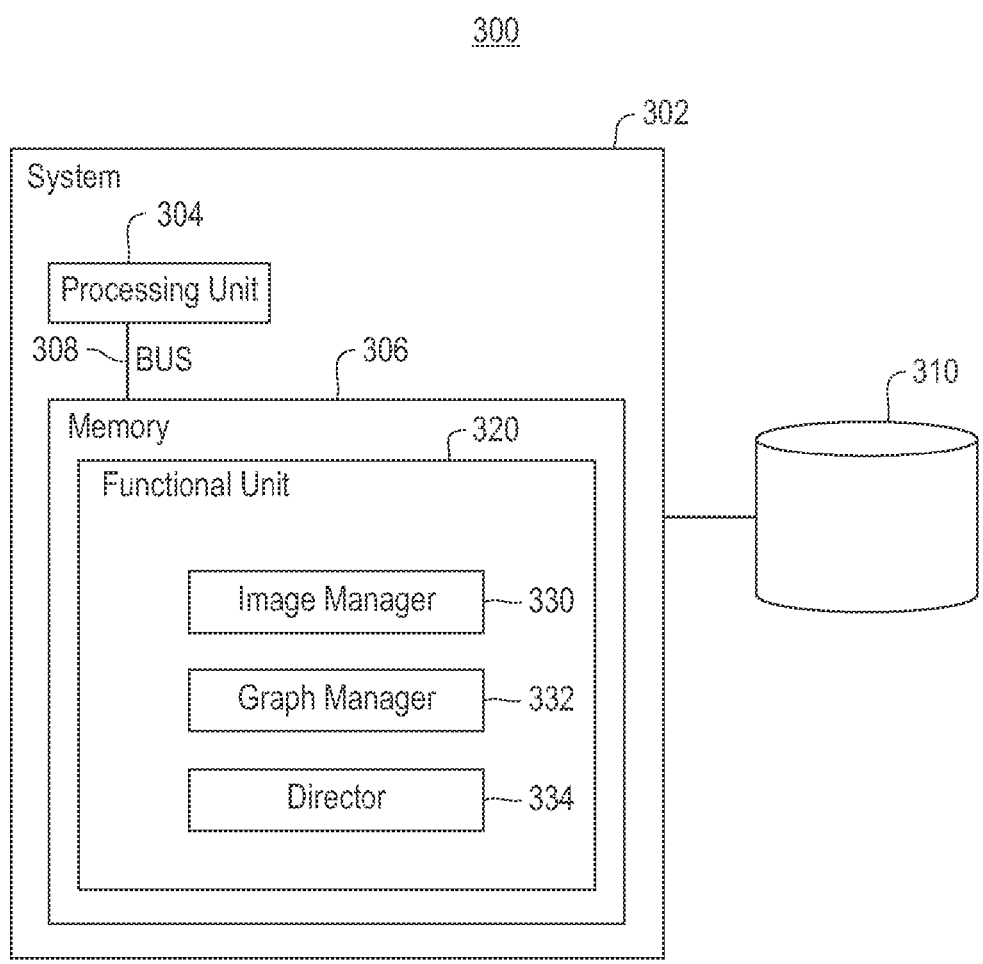
FIG. 3 is a block diagram illustrating tools embedded in a computer system to support construction of a gene interaction network based upon identified image based similarities.

As demonstrated in the flow charts of FIGS. 1 and 2, three dimensional gene image data is evaluated, ranked, and organized in a directed acyclic graph representing the relationship among the extracted data. More specifically, the graph connects the respective genes of related image stacks in a commonly ranking list. FIG. 3 is a block diagram (300) illustrating tools embedded in a computer system to support construction of the gene interaction network and specifically, construction of the directed acyclic graph. A computer system (302) is shown with a processing unit (304) in communication with memory (306) across a bus (308) and in communication with data storage (310). In one embodiment, the data storage (310) is remotely accessed across a network (not shown). A functional unit (320) is provided in communication with the memory (306). The functional unit (320) is provided to construct a gene interaction network. More specifically, the functional unit (320) includes a plurality of managers and a director to support the construction, including an image manager (330), a graph manager (332), and a director (334). The image manager (330) functions to receive recorded images of groups of cells associated with a first set of genes. Each of the groups of cells is received by knocking down one or more genes from a second set of genes. The first and second sets of genes include common genes. Accordingly, recorded images of groups of cells are received by the image manager (330).

Following receipt of the images by the image manager (330), the director (334) computes a gene relationship measure based upon the cellular images and using a morphological similarity measure between corresponding groups of cells. The director (334) ranks image collections having a similar morphology. In one embodiment, the director (334) captures the similarity by modeling a three dimensional shape of a cellular image stack produced by knocking down respective genes. Similarly, in one embodiment, the director (336) partitions a Bayesian network into functional modules that correspond to sets of genes that are part of the same biological pathway based on morphological similarity. The graph manager (332), which is in communication with the director (334), functions to construct a graph for related image stacks and to connect respective genes in the related stacks. In one embodiment, the graph is a directed acyclic graph formed by a collection of vertices, also referred to herein as nodes, and directed edges. Each gene is represented in the graph as a node. The graph manager (332) draws edges between all nodes in the graph whose corresponding images stacks are present in a commonly ranked list. Accordingly, a graph is constructed to represent a ranking list of image collections having a similar morphology, with the images representative of a three dimensional shape of a cellular image stack of genes.

Once the graph is created, the graph manager (332) further defines an interaction network of the genes represented in the graph. The graph manager (332) applies a weight to each edge in the constructed graph. The weight reflects a similarity score and rank in a list of matches for a three dimensional query stack generated for a particular gene. Accordingly, the edge between nodes is created for image stacks in a commonly ranked list, with each edge having an applied weight.

As identified above, the image manager (330), graph manager (332), and director (334) function to construct a gene interaction network with the connectivity of genes represented by nodes and associated edges. The managers and director are shown residing in memory (306) in communication with a processor (304). More specifically, image manager (330), graph manager (332), and director (334) each reside in the functional unit (320) local to memory (306). In one embodiment, the image manager (330), graph manager (332), and director (334) may reside as hardware tools external to memory (306), or they may be implemented as a combination of hardware and software. Similarly, in one embodiment, the managers and the director may be combined into a single functional item that incorporates the functionality of the separate items. As shown herein, each of the managers and the director is shown local to a single processing unit (304). However, in one embodiment the managers and the director may be collectively or individually distributed across a network and function as a unit to construct a gene interaction network. Accordingly, the managers and the director may be implemented as software tools, hardware tools, or a combination of software and hardware tools, to collect and organize data content.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++, Matlab or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 4:
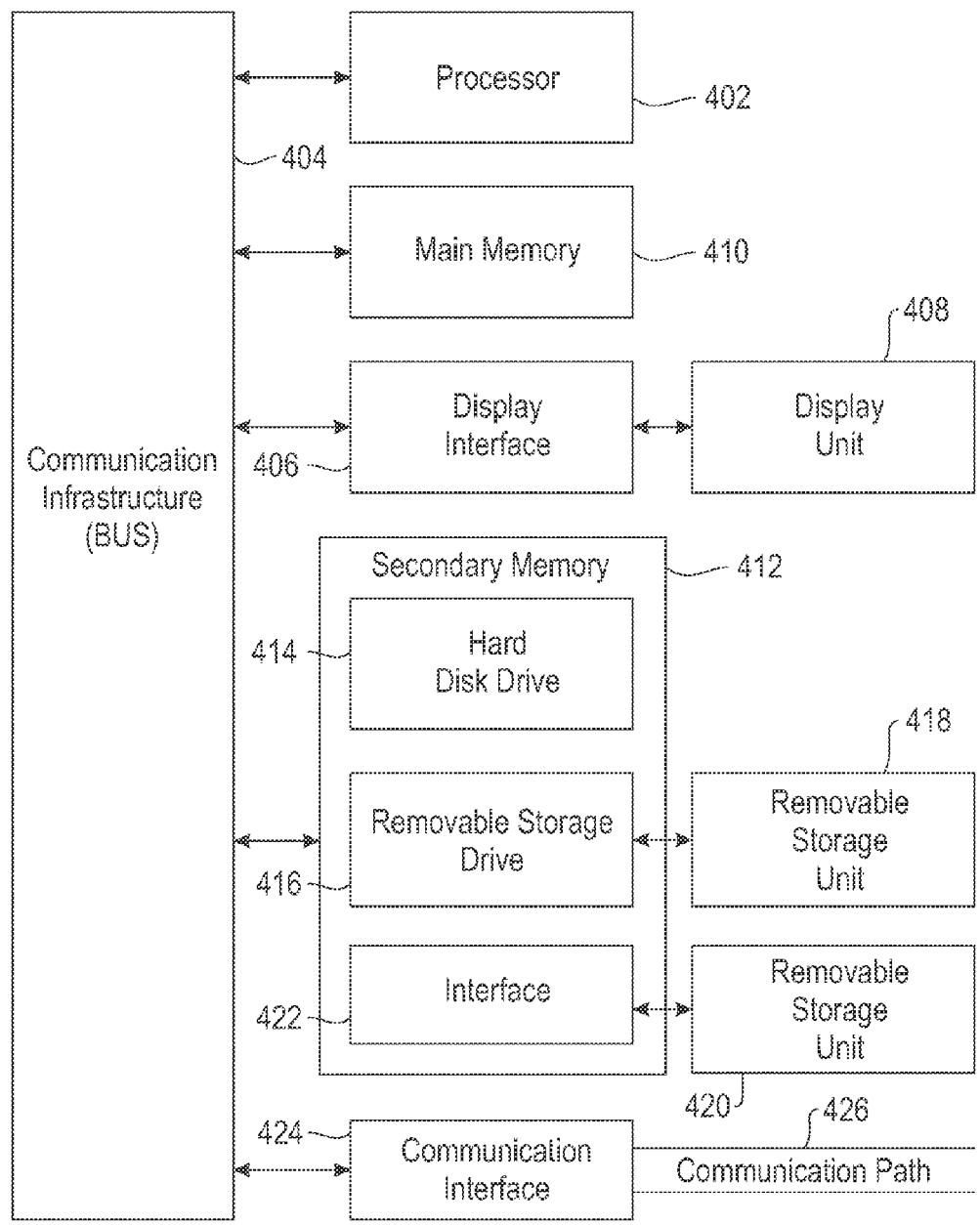
FIG. 4 is a block diagram showing system for implementing an embodiment of the present invention.

Referring now to FIG. 4 is a block diagram showing a system for implementing an embodiment of the present invention. The computer system includes one or more processors, such as a processor (402). The processor (402) is connected to a communication infrastructure (404) (e.g., a communications bus, cross-over bar, or network). The computer system can include a display interface (406) that forwards graphics, text, and other data from the communication infrastructure (404) (or from a frame buffer not shown) for display on a display unit (408). The computer system also includes a main memory (410), preferably random access memory (RAM), and may also include a secondary memory (412). The secondary memory (412) may include, for example, a hard disk drive (414) and/or a removable storage drive (416), representing, for example, a floppy disk drive, a magnetic tape drive, or an optical disk drive. The removable storage drive (416) reads from and/or writes to a removable storage unit (418) in a manner well known to those having ordinary skill in the art. Removable storage unit (418) represents, for example, a floppy disk, a compact disc, a magnetic tape, or an optical disk, etc., which is read by and written to by removable storage drive (416). As will be appreciated, the removable storage unit (418) includes a computer readable medium having stored therein computer software and/or data.

In alternative embodiments, the secondary memory (412) may include other similar means for allowing computer programs or other instructions to be loaded into the computer system. Such means may include, for example, a removable storage unit (420) and an interface (422). Examples of such means may include a program package and package interface (such as that found in video game devices), a removable memory chip (such as an EPROM, or PROM) and associated socket, and other removable storage units (420) and interfaces (422) which allow software and data to be transferred from the removable storage unit (420) to the computer system.

The computer system may also include a communications interface (424). Communications interface (424) allows software and data to be transferred between the computer system and external devices. Examples of communications interface (424) may include a modem, a network interface (such as an Ethernet card), a communications port, or a PCMCIA slot and card, etc. Software and data transferred via communications interface (424) are in the form of signals which may be, for example, electronic, electromagnetic, optical, or other signals capable of being received by communications interface (424). These signals are provided to communications interface (424) via a communications path (i.e., channel) (426). This communications path (426) carries signals and may be implemented using wire or cable, fiber optics, a phone line, a cellular phone link, a radio frequency (RF) link, and/or other communication channels.

In this document, the terms "computer program medium," "computer usable medium," and "computer readable medium" are used to generally refer to media such as main memory (410) and secondary memory (412), removable storage drive (416), and a hard disk installed in hard disk drive (414). Computer programs (also called computer control logic) are stored in main memory (410) and/or secondary memory (412). Computer programs may also be received via a communication interface (424). Such computer programs, when run, enable the computer system to perform the features of the present invention as discussed herein. In particular, the computer programs, when run, enable the processor (402) to perform the features of the computer system. Accordingly, such computer programs represent controllers of the computer system.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Alternative Embodiment

It will be appreciated that, although specific embodiments of the invention have been described herein for purposes of illustration, various modifications may be made without departing from the spirit and scope of the invention. Accordingly, the scope of protection of this invention is limited only by the following claims and their equivalents.

We claim:

1. A system comprising:
   a processor in communication with memory and data storage;
   the processor programmed to construct a gene interaction network including the processor to:
   generate a cellular image stack via RNAi screening of a set of genes, wherein the generation comprises receipt of recorded images of groups of cells associated with a first set of genes, wherein each of the groups is received by knocking down one or more genes from a second set of genes and wherein the first set of genes and the second set of genes include common genes;
   store the generated cellular image stack in the memory;
   create a set of three-dimensional feature vectors from the stored cellular image data;
   compare the stored cellular image data, based on the set of feature vectors, and produce a gene relationship measure including computing the gene relationship measure using a morphological similarity measure between the corresponding groups of cells reflecting structural similarities between the images being compared;
   convert the gene relationship measure into a ranking of images with similar morphology, including modeling a three-dimensional shape of the cellular image stack produced by knocking down respective genes;
   construct a graph for related image stacks, draw edges between all nodes of the graph based on the image ranking being in a commonly ranked list, and apply a weight to each edge based on node similarity, wherein each gene is a node in the graph; and
   output the graph to the processor.

2. The system of claim 1, wherein the weight reflects a similarity score between nodes for a three dimensional query stack generated for a particular gene.

3. The system of claim 2, further comprising the processor to partition a Bayesian network into functional modules that correspond to sets of genes that are part of a same biological pathway based on morphological similarity.

4. The system of claim 1, wherein the graph is directed.

5. The system of claim 4, wherein the graph is acyclic.

6. A computer program product for constructing a gene interaction network, the computer program product comprising a computer readable storage medium having program code embodied therewith, the program code executable by a processor to:
   generate a cellular image stack via RNAi screening of a set of genes, wherein the generation comprises receipt of recorded images of groups of cells associated with a first set of genes, wherein each of the groups is received by knocking down one or more genes from a second set of genes and wherein the first set of genes and the second set of genes include common genes;
   store the generated cellular image stack in the memory;
   create a set of three-dimensional feature vectors from the stored cellular image data;
   compare the stored cellular image data, based on the set of feature vectors, and produce a gene relationship measure including computing the gene relationship measure using a morphological similarity measure between the corresponding groups of cells reflecting structural similarities between the images being compared;
   convert the gene relationship measure into a ranking of images with similar morphology, including modeling a three-dimensional shape of the cellular image stack produced by knocking down respective genes;
   construct a graph for related image stacks, draw edges between all nodes of the graph based on the image ranking being in a commonly ranked list, and apply a weight to each edge based on node similarity, wherein each gene is a node in the graph; and
   output the graph to the processor.

7. The computer program product of claim 6, wherein the weight reflects a similarity score between nodes for a three dimensional query stack generated for a particular gene.

8. The computer program product of claim 7, further comprising program code to partition a Bayesian network into functional modules that correspond to sets of genes that are part of a same biological pathway based on morphological similarity.

9. The computer program product of claim 6, wherein the graph is directed.

10. The computer program product of claim 9, wherein the graph is acyclic.

* * * * *